US012571407B1

(12) United States Patent
Bao

(10) Patent No.: US 12,571,407 B1
(45) Date of Patent: Mar. 10, 2026

(54) REFRIGERABLE HANGING ICE NECK COLLAR

(71) Applicant: Shenzhen Keeway Technology Co., Ltd., Shenzhen (CN)

(72) Inventor: Guoqiang Bao, Shenzhen (CN)

(73) Assignee: Shenzhen Keeway Technology Co.,Ltd., Shenzhen (CN)

( * ) Notice: Subject to any disclaimer, the term of this patent is extended or adjusted under 35 U.S.C. 154(b) by 0 days.

(21) Appl. No.: 19/173,420

(22) Filed: Apr. 8, 2025

(30) Foreign Application Priority Data

Dec. 17, 2024 (CN) .......................... 202423128241.2

(51) Int. Cl.
| | |
|---|---|
| *F04D 29/42* | (2006.01) |
| *A61F 7/00* | (2006.01) |
| *F04D 29/44* | (2006.01) |
| *F04D 29/58* | (2006.01) |

(52) U.S. Cl.
CPC ............ *F04D 29/4226* (2013.01); *A61F 7/00* (2013.01); *F04D 29/441* (2013.01); *F04D 29/582* (2013.01); *A61F 2007/0011* (2013.01)

(58) Field of Classification Search
CPC .. F04D 29/4226; F04D 29/441; F04D 29/582; A61F 7/00; A61F 2007/0011
See application file for complete search history.

(56) References Cited

U.S. PATENT DOCUMENTS

| | | | | |
|---|---|---|---|---|
| 5,802,865 A * | 9/1998 | Strauss | ..................... | A61F 7/10 62/259.3 |
| 6,682,552 B2 * | 1/2004 | Ramsden | ................. | A61F 7/10 607/114 |

| | | | | |
|---|---|---|---|---|
| 11,624,370 B2 * | 4/2023 | Liu | ........................ | F04D 29/582 415/203 |
| 11,703,060 B1 * | 7/2023 | Song | ..................... | F04D 25/166 415/60 |
| 11,815,098 B1 * | 11/2023 | Patil | ........................ | F25B 21/02 |

(Continued)

FOREIGN PATENT DOCUMENTS

| | | | | |
|---|---|---|---|---|
| CN | 111557775 A | * | 8/2020 | ........... A61N 5/0625 |
| CN | 111558159 A | * | 8/2020 | ......... A61N 1/36014 |

(Continued)

OTHER PUBLICATIONS

Mun et al. KR 20200117635 Espacenet—English Machine Translation (Year: 2020).*

*Primary Examiner* — Nathaniel E Wiehe
*Assistant Examiner* — Wayne A Lambert
(74) *Attorney, Agent, or Firm* — Westbridge IP LLC

(57) ABSTRACT

Disclosed is a refrigerable hanging ice neck collar, which includes a neck collar bracket, a heat dissipation component, a refrigeration sheet, a fan, a non-metallic shell, a cold storage material layer and an electronic control component. The neck collar bracket and the non-metallic shell are respectively elastic, and the electronic control component is used to control the cooling of the refrigeration sheet and the rotation of the fan. The fan rotates to supply air into the air duct, and the through hole in the air duct is used to connect the heat dissipation component. When the wind in the air duct passes through the through hole, it will take away part of the heat of the refrigeration sheet and dissipate heat and cool the refrigeration sheet, and the air outlet can also provide airflow to blow toward the head.

9 Claims, 6 Drawing Sheets

(56) References Cited

U.S. PATENT DOCUMENTS

| | | | | |
|---|---|---|---|---|
| 2011/0259028 A1* | 10/2011 | Lee | ........................ | A61F 7/0085 |
| | | | | 165/59 |
| 2017/0370596 A1* | 12/2017 | Lee | ........................ | A42B 3/286 |
| 2020/0187574 A1* | 6/2020 | Te Hsiang | ......... | A41D 13/0053 |
| 2021/0355959 A1* | 11/2021 | Liu | ..................... | F04D 25/0673 |
| 2021/0355960 A1* | 11/2021 | Liu | ..................... | F04D 25/0673 |
| 2022/0065258 A1* | 3/2022 | Liu | ........................ | A42B 3/286 |
| 2023/0193910 A1* | 6/2023 | Liu | ....................... | F04D 25/084 |
| | | | | 415/203 |
| 2025/0059980 A1* | 2/2025 | Chen | .................. | F04D 29/4226 |

FOREIGN PATENT DOCUMENTS

| | | | | | |
|---|---|---|---|---|---|
| KR | 20200058926 A | * | 5/2020 | ............. | A61F 7/007 |
| KR | 20200117635 A | * | 10/2020 | ........... | A61N 5/0616 |
| KR | 20230155077 A | * | 11/2023 | ............. | F04D 25/16 |

* cited by examiner

REFRIGERABLE HANGING ICE NECK COLLAR

CROSS-REFERENCE TO RELATED APPLICATIONS

The present application claims priority to Chinese Patent Application No. 202423128241.2, filed on Dec. 17, 2024, the entire contents of which are incorporated herein by reference.

TECHNICAL FIELD

The present application relates to the technical field of refrigeration equipment, in particular to a refrigerable hanging ice neck collar.

BACKGROUND

Currently, the cooling collars on the market that use phase change materials or other gel materials as fillers usually only use the material's own characteristics to store cold, and the amount of cold storage is relatively limited. After using it for a period of time, it needs to be left to store cold naturally or put in the refrigerator to store cold, which is not a good experience. Therefore, another type of collar product that uses refrigeration sheets for cooling has appeared on the market. This collar product absorbs heat through the contact of the shell with the skin, and transfers the heat to the refrigeration sheet to achieve cooling. However, the cooling efficiency of only using the refrigeration sheet is not high enough. When a lot of heat accumulates at the refrigeration sheet, the cooling effect of the collar product will be significantly reduced.

SUMMARY

The main purpose of the present application is to provide a refrigerable hanging ice neck collar, aiming to solve the problem that the existing neck hanging products only cool down by refrigeration sheets, and the cooling efficiency is not high, and when more heat accumulates, the cooling effect of the neck hanging product will be significantly reduced.

In order to achieve the above-mentioned purpose, the present application proposes a refrigerable hanging ice neck collar, which includes an elastic neck collar bracket, a heat dissipation component, a refrigeration sheet, a fan, a non-metallic shell, a cold storage material layer and an electronic control component.

In an embodiment, the heat dissipation component is provided at the neck collar bracket and is configured to form an internal air duct. A side of the air duct is provided with a through hole, and the heat dissipation component is provided with an air inlet and an air outlet.

In an embodiment, the refrigeration sheet is provided at an external side of the heat dissipation component and is configured to cover the through hole.

In an embodiment, the fan is provided at an end of the neck collar bracket and is adjacent to the air inlet of the heat dissipation component. An air outlet direction of the fan is oriented toward the air inlet.

In an embodiment, the elastic non-metallic shell is provided at an inner side of the neck collar bracket. A portion of the non-metallic shell is connected to a side of the heat dissipation component, and the non-metallic shell is provided with a material filling part.

In an embodiment, the cold storage material layer is provided within the material filling part of the non-metallic shell, and is configured to contact both the refrigeration sheet and an inner side of the non-metallic shell.

In an embodiment, the electric control component is provided at the neck collar bracket and is electrically connected to the refrigeration sheet and the fan.

In an embodiment, the end of the neck collar bracket is provided with a protective shell for protecting the fan, and the protective shell is provided with an air intake side and an air exhaust side. The air exhaust side of the protective shell is connected and communicated with one end of the heat dissipation component where the air inlet is provided. The fan is provided within the protective shell, and the air outlet direction of the fan is toward the air exhaust side of the protective shell.

In an embodiment, the air intake side of the protective shell is provided with a steel mesh, and the fan is provided at a side of the steel mesh proximate to the air inlet.

In an embodiment, two fans are provided, and the two fans are respectively provided at two ends of the neck collar bracket. Two heat dissipation components are provided at the neck collar bracket, and each of heat dissipation components is provided with a corresponding refrigeration sheet. The air inlets of the two heat dissipation components respectively correspond to the two fans.

In an embodiment, a plurality of refrigeration sheets are evenly distributed on the heat dissipation component.

In an embodiment, the heat dissipation component includes a heat dissipation fin and a heat dissipation bracket. The neck collar bracket is provided with a bayonet, and the heat dissipation bracket is provided at the inner side of the neck collar bracket. The heat dissipation fin is provided within the bayonet and is configured to seal the bayonet, forming the air duct cooperatively with the neck collar bracket and the heat dissipation bracket. The heat dissipation fin is opposite to the through hole and the refrigeration sheet.

In an embodiment, a protrusion is provided at a side of the heat dissipation fin within the air duct, and the protrusion is configured to extend through the through hole and contact a side of the refrigeration sheet.

In an embodiment, along an air inlet direction of the air inlet, a plurality of guide grooves are provided at an inner side of the heat dissipation bracket, a plurality of guide holes are provided in the heat dissipation fin, and each guide hole is communicated with the corresponding guide groove.

In an embodiment, a plurality of air outlets are provided, and each of the air outlets is communicated with a corresponding airflow guide groove.

In an embodiment, an installation compartment is provided at an inner side of the neck collar bracket, the electric control component is provided within the installation compartment, and an end of the heat dissipation component away from the air inlet is connected to a side of the installation compartment.

The present application provides a refrigerable hanging ice neck collar including a neck collar bracket, a heat dissipation component, a refrigeration sheet, a fan, a non-metallic shell, a cold storage material layer and an electronic control component. The neck collar bracket and the non-metallic shell are elastic, so as to facilitate the refrigerable hanging ice neck collar to be stretched out and put on the neck or stretched out and taken off the neck. The electronic control component is used to control the cooling of the refrigeration sheet and the rotation of the fan, and the fan rotates to supply air into the air duct. The wind in the air duct will take away part of the heat of the refrigeration sheet when passing through the through hole and dissipate the heat and cool the refrigeration sheet, thereby enhancing the continuous cooling capacity of the refrigeration sheet. The air outlet can also provide airflow to blow toward the head to help cool down, thereby improving the cooling effect of the refrigerable hanging ice neck collar. At the same time, the refrigeration sheet in the present application transfers the cold to the non-metallic shell through the cold storage material layer, and the cold storage material layer can also accumulate a certain amount of cold. When the electronic control component is turned off, the cold storage material layer can continue to cool for a period of time. When the cooling temperature of the cold storage material layer is not enough, the electronic control component can be turned on again to control the refrigeration sheet to continue cooling to adjust the temperature of the cold storage material layer. Compared with metal refrigeration, the non-metallic shell is more gentle and less irritating.

BRIEF DESCRIPTION OF THE DRAWINGS

In order to more clearly illustrate the embodiments of the present application or the technical solutions in the related art, the drawings required for use in the embodiments or the description of the related art will be briefly introduced below. Obviously, the drawings described below are only some embodiments of the present application. For persons skilled in the art, other drawings can be obtained based on the structures shown in these drawings without paying creative efforts.

Figure 1:
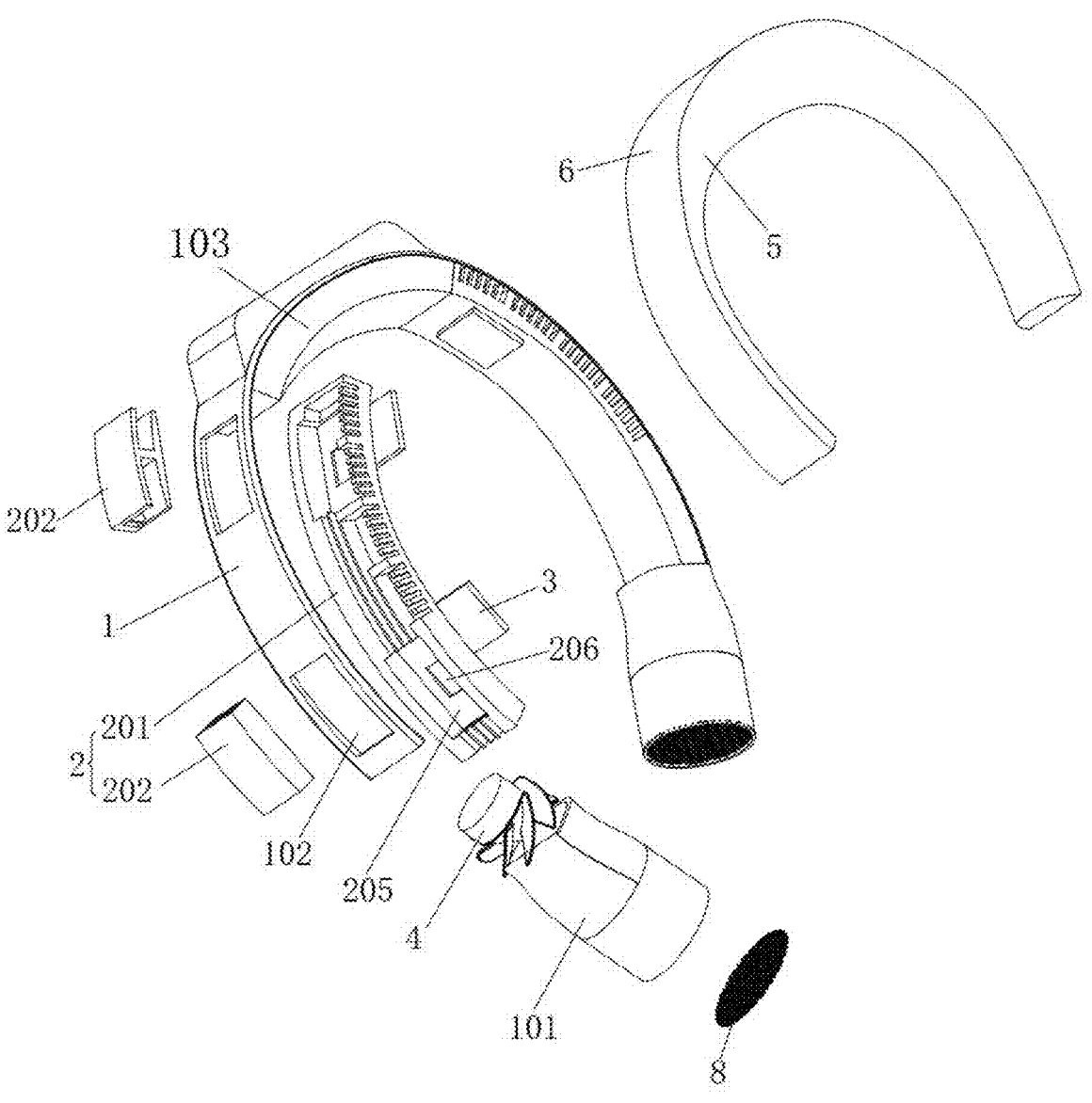
FIG. 1 is an exploded view of a refrigerable hanging ice neck collar according to an embodiment of the present application.

The realization of the purpose, functional features and advantages of the present application will be further explained in conjunction with embodiments and with reference to the drawings.

DETAILED DESCRIPTION OF THE EMBODIMENTS

The following will be combined with the drawings in the embodiments of the present application to clearly and completely describe the technical solutions in the embodiments of the present application. Obviously, the described embodiments are only part of the embodiments of the present application, not all of the embodiments. Based on the embodiments of the present application, all other embodiments obtained by persons skilled in the art without creative efforts are within the scope of the present application.

It should be noted that if the embodiments of the present application involve directional indications (such as up, down, left, right, front, back . . . ), the directional indications are only used to explain the relative position relationship, movement status, etc. between the components in a certain specific posture. If the specific posture changes, the directional indications will also change accordingly.

In addition, if there are descriptions involving "first", "second", etc. in the embodiments of the present application, the descriptions of "first", "second", etc. are only used for descriptive purposes and cannot be understood as indicating or implying their relative importance or implicitly indicating the number of technical features indicated. Therefore, the features limited to "first" and "second" may explicitly or implicitly include at least one of the features. In addition, if "and/or" appears in the full text, its meaning includes three parallel solutions. Taking "A and/or B" as an example, it includes solution A, solution B, or solutions that satisfy both A and B. In addition, the technical solutions between the various embodiments can be combined with each other, but it must be based on the ability of persons skilled in the art to implement. When the combination of technical solutions is contradictory or cannot be implemented, it should be deemed that such combination of technical solutions does not exist and is not within the scope of the present application.

Currently, the cooling collars on the market that use phase change materials or other gel materials as fillers usually only use the material's own characteristics to store cold, and the amount of cold storage is relatively limited. After using it for a period of time, it needs to be left to store cold naturally or put in the refrigerator to store cold, which is a poor experience. Therefore, another type of collar product that uses a refrigeration sheet for cooling has appeared on the market. This collar product absorbs heat through the shell contacting the skin, and transfers the heat to the refrigeration sheet to achieve cooling. However, the cooling efficiency of only using the refrigeration sheet is not high enough. When a lot of heat accumulates at the refrigeration sheet, the cooling effect of the collar product will be significantly reduced. In addition, the collar products on the market usually use a metal shell in contact with the skin. Although the metal shell has a good cooling effect, it is too irritating to the skin.

Therefore, the present application proposes a refrigerable hanging ice neck collar to solve the above problems.

Figure 2:
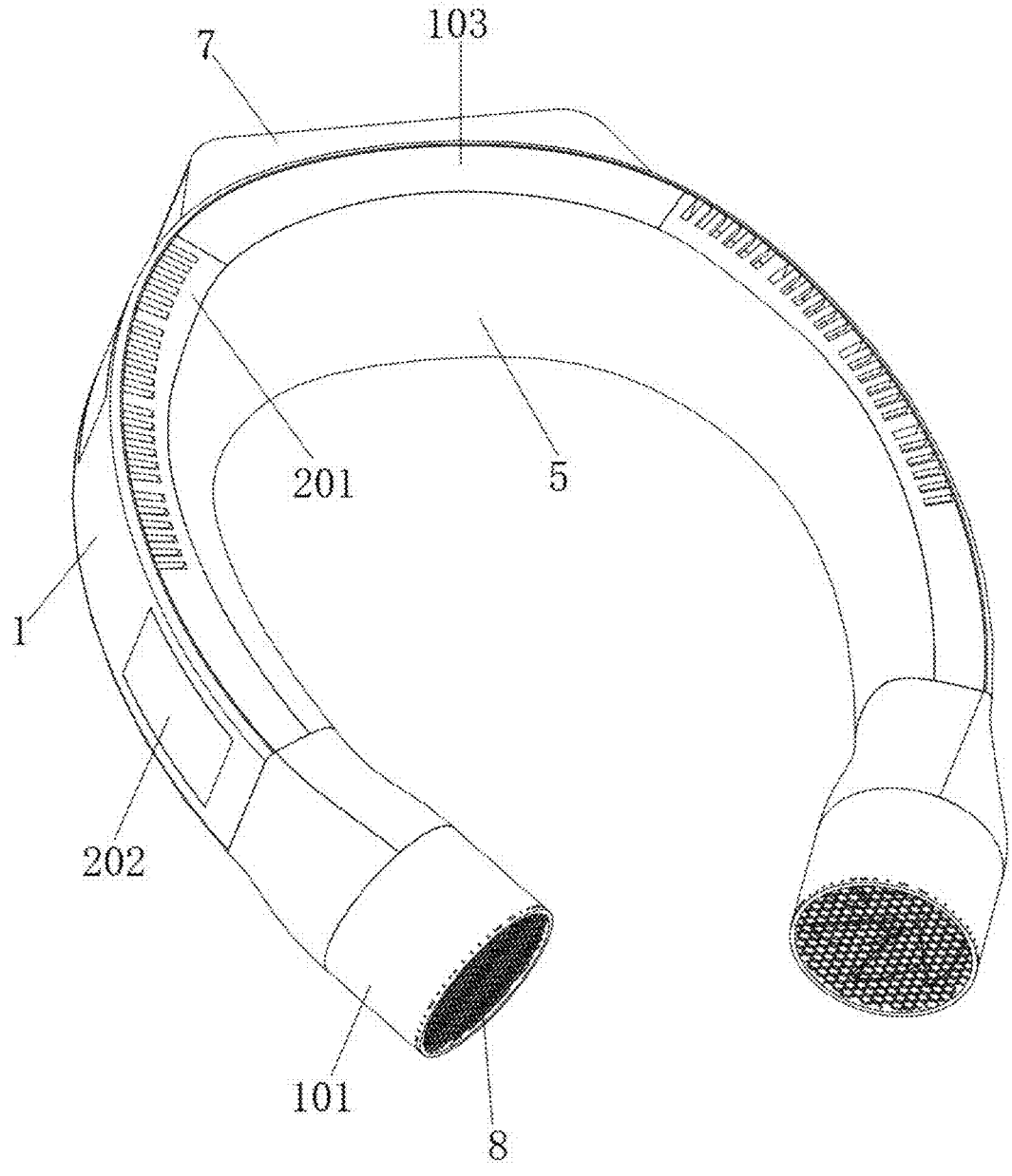
FIG. 2 is a schematic structural diagram of a refrigerable hanging ice neck collar according to an embodiment of the present application.
Figure 3:
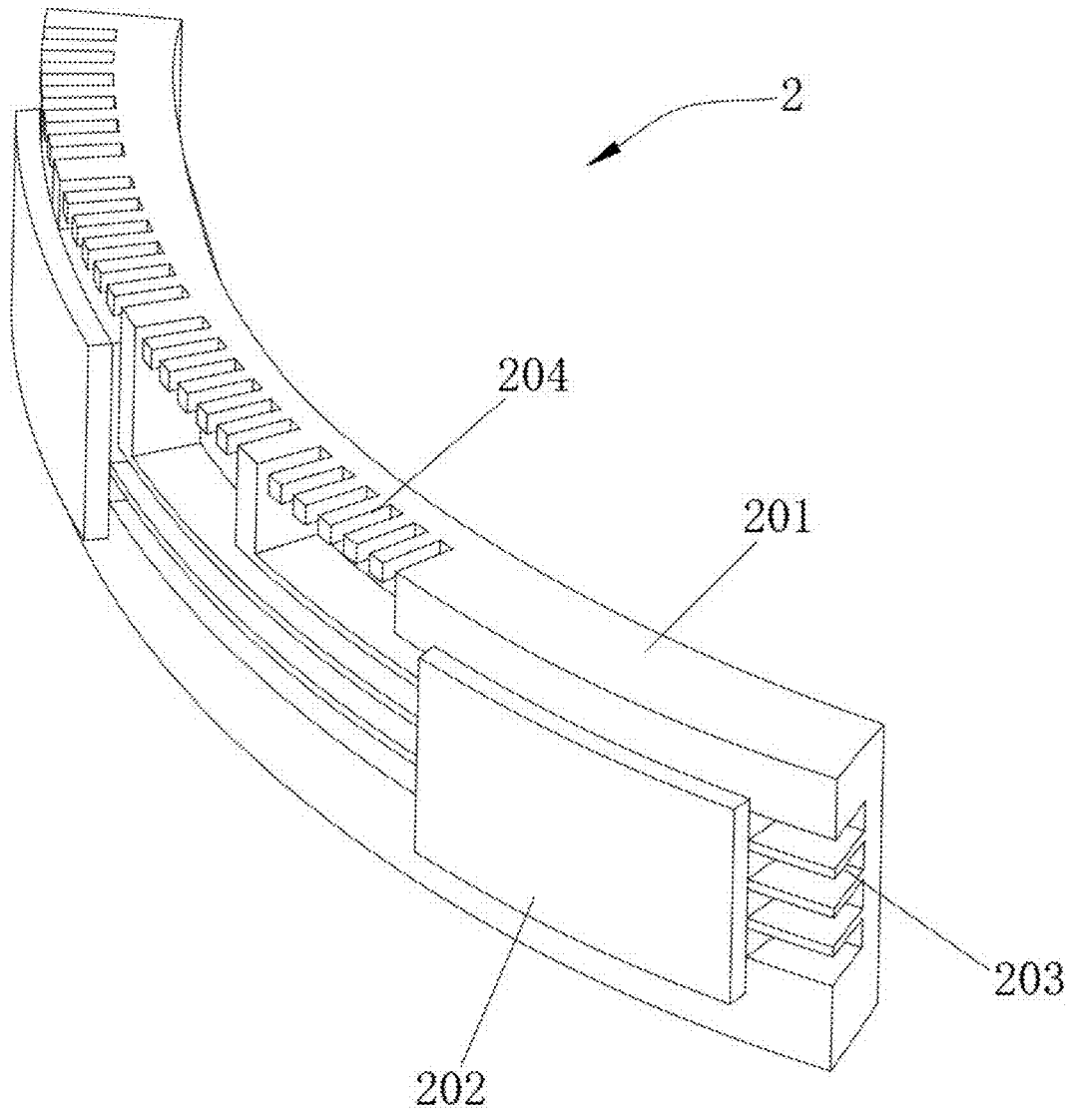
FIG. 3 is a schematic structural diagram of a heat dissipation component according to an embodiment of the present application.

As shown in FIG. 1 to FIG. 3, in an embodiment of the present application, the refrigerable hanging ice neck collar includes an elastic neck collar bracket 1, a heat dissipation component 2, a refrigeration sheet 3, a fan 4, a non-metallic shell 5, a cold storage material layer 6, and an electronic control component 7. The heat dissipation component 2 is arranged on the neck collar bracket 1 and forms an air duct 205 inside, a through hole 206 is provided on one side of the air duct 205, and the heat dissipation component 2 is provided with an air inlet 203 and an air outlet 204. The refrigeration sheet 3 is arranged on the outer side of the heat dissipation component 2 and covers the through hole 206. The fan 4 is arranged at the end of the neck collar bracket 1 and close to the air inlet 203 of the heat dissipation component 2, and the air outlet direction of the fan 4 is toward the air inlet 203. A non-metallic shell 5 is elastic and is arranged on one side of the inner side of the neck collar bracket 1, a part of the non-metallic shell 5 is connected to one side of the heat dissipation component 2, and the non-metallic shell 5 has a material filling part. The cold storage material layer 6 is arranged in the material filling part of the non-metallic shell 5 and is in contact with the refrigeration sheet 3 and the inner side of the non-metallic shell 5. The electronic control component 7 is arranged on the neck collar bracket 1 and is electrically connected to the refrigeration sheet 3 and the fan 4.

In this embodiment, the refrigerable hanging ice neck collar includes a neck collar bracket 1, a heat dissipation component 2, a refrigeration sheet 3, a fan 4, a non-metallic shell 5, a cold storage material layer 6 and an electronic control component 7. The neck collar bracket 1 and the non-metallic shell 5 are respectively elastic, and the cold storage material layer 6 is a flexible layer, so that the refrigerable hanging ice neck collar can be stretched out and put on the neck or stretched out and taken off the neck. The heat dissipation component 2 is arranged on the neck collar bracket 1 and forms an air duct 205 inside, a through hole 206 is provided on one side of the air duct 205, and the heat dissipation component 2 is provided with an air inlet 203 and an air outlet 204. The refrigeration sheet 3 is arranged on the outer side of the heat dissipation component 2 and covers the through hole 206, so that the wind in the air duct 205 can take away part of the heat of the refrigeration sheet 3 and send it out from the air outlet 204. The fan 4 is arranged at the end of the neck collar bracket 1 and close to the air inlet 203 of the heat dissipation component 2, and the air outlet direction of the fan 4 is toward the air inlet 203, which is used for blowing air into the heat dissipation component 2. The non-metallic shell 5 has a material filling part (not shown), and the side of the non-metallic shell 5 provided with the material filling part is sealingly connected to the inner side of the neck collar bracket 1 and one side of the heat dissipation component 2. The cold storage material layer 6 is arranged in the material filling part of the non-metallic shell 5, and is in contact with the refrigeration sheet 3 and the inner side of the non-metallic shell 5, so as to transfer the cold of the refrigeration sheet 3 to the non-metallic shell 5. The electric control component 7 is arranged on the neck collar bracket 1 and is electrically connected to the refrigeration sheet 3 and the fan 4, and is used to control the opening or closing of the refrigeration sheet 3 and the fan 4. The electric control component 7 is an existing device, such as a combination of a switch, a control circuit board and a battery. If the refrigeration sheet 3 and the fan 4 are controlled separately, two switches can be set, and if they are controlled simultaneously, one switch can be selected for control. Therefore, in this embodiment, after the fan 4 rotates, air is supplied into the air duct 205. When the wind in the air duct 205 passes through the through hole 206, it will take away part of the heat of the refrigeration sheet 3 and dissipate heat and cool the refrigeration sheet 3, thereby enhancing the continuous cooling ability of the refrigeration sheet 3 and improving the cooling effect of the refrigerable hanging ice neck collar. At the same time, the refrigeration sheet 3 in the present application transfers the cold to the non-metallic shell 5 through the cold storage material layer 6. The cold storage material layer 6 can also accumulate a certain amount of cold. When the electric control component 7 is turned off, the cold storage material layer 6 can continue to cool for a period of time. When the cooling temperature of the cold storage material layer 6 is not enough, the electric control component 7 can be turned on again to control the refrigeration sheet 3 to continue cooling to adjust the temperature of the cold storage material layer 6. Compared with metal cooling, the non-metallic shell 5 has a milder effect and less irritation. After the present application combines the refrigeration sheet 3 with the cold storage material layer 6, the function of temperature adjustment is realized. Compared with the related art products with only the refrigeration sheet 3 for refrigeration, it has better cold storage capacity. After the refrigeration sheet 3 is turned off, the refrigeration effect can be maintained for a period of time, which reduces energy consumption and cost, reduces irritation to the skin, and enhances comfort and practicality.

Furthermore, a protective shell 101 for protecting the fan 4 is provided at the end of the neck collar bracket 1, and the protective shell 101 has an air intake side and an air exhaust side. The air exhaust side of the protective shell 101 is connected and communicated with one end of the heat dissipation component 2 where the air inlet 203 is provided. The fan 4 is arranged in the protective shell 101, and the air outlet direction of the fan 4 is toward the air exhaust side of the protective shell 101. Specifically, a protective shell 101 for hiding the fan 4 is provided at the end of the neck collar bracket 1. The protective shell 101 can be cylindrical, square or irregular. The shape of the protective shell 101 is not limited. The protective shell 101 and the end of the neck collar bracket 1 can be connected in a fixed manner or a detachable manner. If it is a fixed connection, the two can be formed as one piece. One end of the protective shell 101 is connected and communicated with one end of the heat dissipation component 2 where an air inlet 203 is provided. The fan 4 is fixedly arranged in the protective shell 101, and the other end of the protective shell 101 leads to the outside. When the fan 4 rotates, air will be blown into the air inlet 203. The protective shell 101 protects and hides the fan 4.

Furthermore, a steel mesh 8 is provided on the air intake side of the protective shell 101, and the fan 4 is arranged on the side of the steel mesh 8 close to the air inlet 203. The steel mesh 8 is used to block foreign matter or larger particles from entering the protective shell 101 to avoid clogging the air duct 205 in the heat dissipation component 2. The steel mesh 8 can further protect the fan 4 and ensure the cooling effect of the refrigerable hanging ice neck collar.

In this embodiment, two fans 4 are provided, and the two fans 4 are respectively provided at the two ends of the neck collar bracket 1. The two fans 4 are respectively electrically connected to the electric control component 7, and the two fans 4 can be simultaneously controlled to start or stop running by the electric control component 7. The neck collar bracket 1 is provided with two heat dissipation components 2, each heat dissipation component 2 is provided with a refrigeration sheet 3, and the air inlets 203 of the two heat dissipation components 2 correspond to the two fans 4 one by one. Specifically, by respectively providing a cooling system formed by a group of heat dissipation component 2, fan 4, and refrigeration sheet 3 on the left and right parts of the neck collar bracket 1, the cooling effect of the refrigerable hanging ice neck collar is further enhanced.

Furthermore, there are multiple refrigeration sheets 3 on the heat dissipation component 2, and the multiple refrigeration sheets 3 are evenly distributed on the heat dissipation component 2, so that the temperature of each part of the non-metallic shell is balanced and the cooling effect is uniform.

Figure 4:
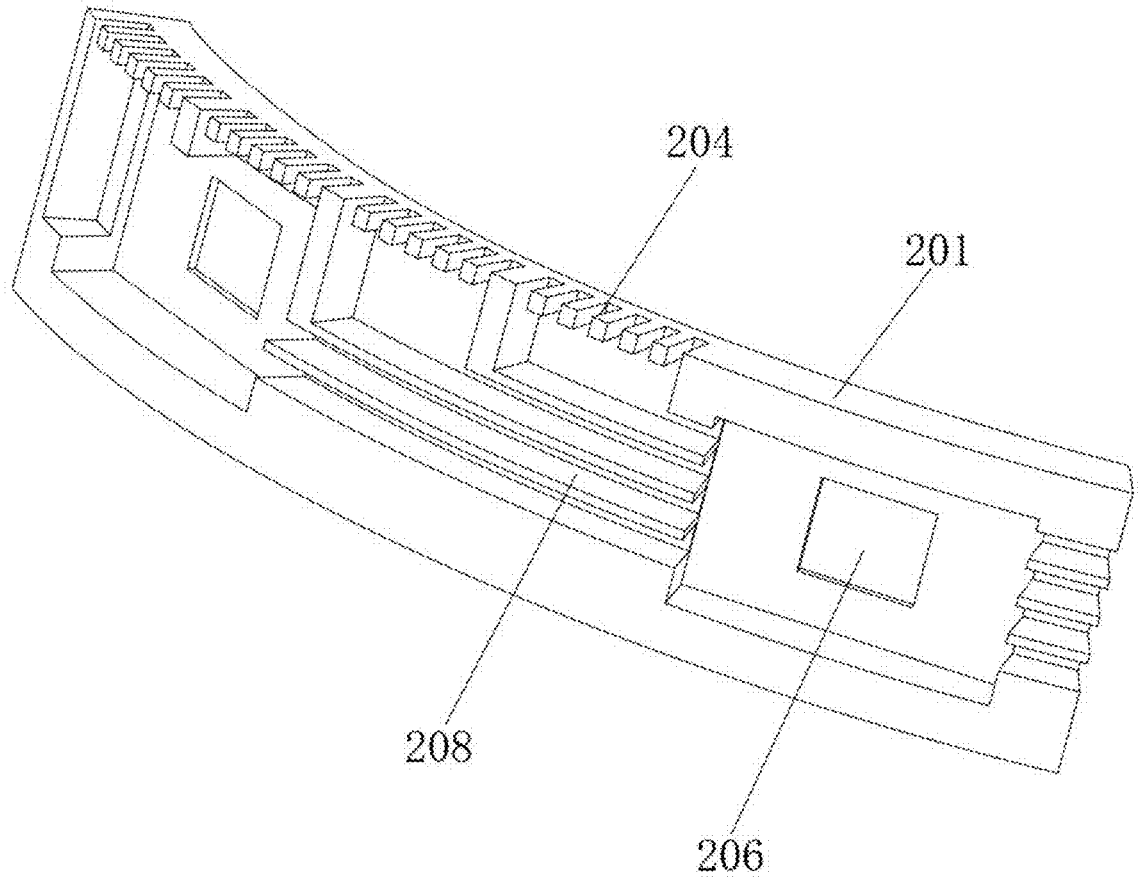
FIG. 4 is a schematic structural diagram of a heat dissipation bracket according to an embodiment of the present application.
Figure 5:
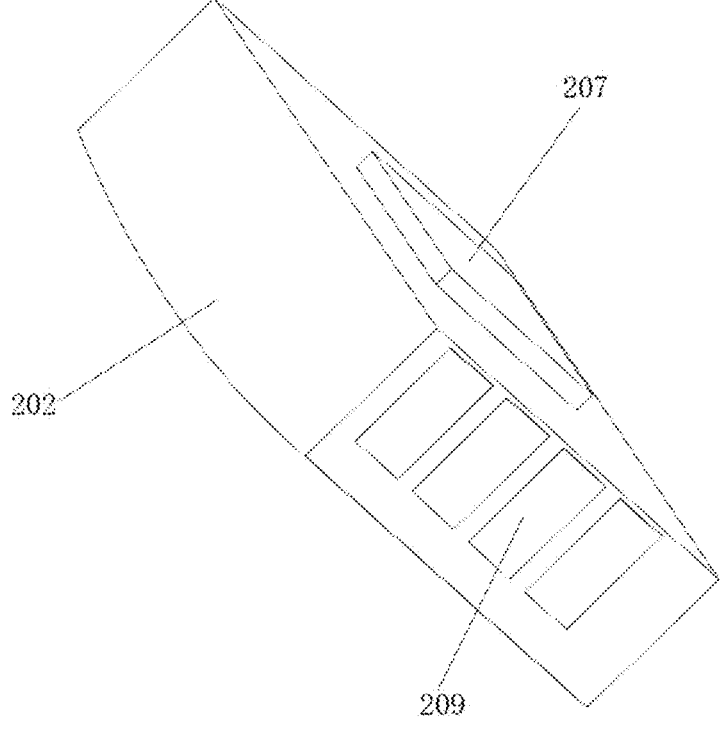
FIG. 5 is a schematic structural diagram of a heat dissipation fin according to an embodiment of the present application.
Figure 6:
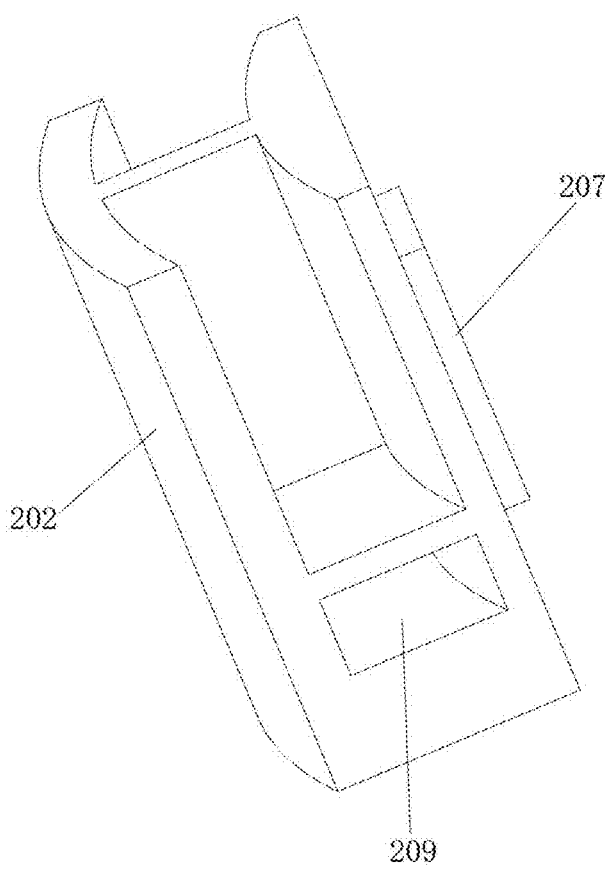
FIG. 6 is a schematic structural diagram of a heat dissipation fin according to another embodiment of the present application.

As shown in FIG. 4 to FIG. 6, further, the heat dissipation component 2 includes a heat dissipation fin 202 and a heat dissipation bracket 201. The neck collar bracket 1 is provided with a bayonet 102, the heat dissipation bracket 201 is arranged on the inner side of the neck collar bracket 1, the heat dissipation fin 202 is arranged in the bayonet 102 and seals the bayonet 102, so as to enclose the neck collar bracket 1 and the heat dissipation bracket 201 and form the air duct 205, and the heat dissipation fin 202 is arranged opposite to the through hole 206 and the refrigeration sheet 3. Specifically, the heat dissipation fin 202 in this embodiment can be detachably connected to the neck collar bracket 1, so that the heat dissipation fin 202 can be removed to dredge the inside of the air duct 205. The heat dissipation bracket 201 in this embodiment is an aluminum bracket, the heat dissipation bracket 201 absorbs the heat of the refrigeration sheet 3 through contact with the refrigeration sheet 3, and the heat dissipation bracket 201 and the refrigeration sheet 3 are cooled simultaneously by the fan 4.

At the same time, a protrusion 207 is provided on one side of the heat dissipation fin 202 located in the air duct 205, and the protrusion 207 penetrates the through hole 206 and contacts one side of the refrigeration sheet 3. Specifically, since the aluminum heat dissipation bracket 201 is large and therefore heavy, the user experience is poor after hanging it on the neck. Therefore, the heat dissipation bracket 201 in this embodiment is a non-metallic bracket and is made of lightweight materials. The heat dissipation fin 202 is an aluminum sheet. The heat dissipation fin 202 contacts the refrigeration sheet 3 through the protrusion 207 to achieve heat transfer, and then the refrigeration sheet 3 and the aluminum sheet are blown by the fan 4 at the same time to dissipate heat, which not only ensures the heat dissipation efficiency but also reduces the overall weight of the collar.

In this embodiment, along the air inlet direction of the air inlet 203, a plurality of guide grooves 208 are provided on the inner side of the heat dissipation bracket 201, and a plurality of guide holes 209 are provided in the heat dissipation fin 202, and each of the guide holes 209 is connected to each of the guide grooves 208 and corresponds to each other. Specifically, each of the guide grooves 208 and each of the guide holes 209 has the same width, and the wind direction is guided by each of the guide grooves 208 and the guide holes 209, so as to avoid the wind in the air duct 205 from running around, thereby improving the heat dissipation efficiency of the heat dissipation fin 202 and the refrigeration sheet 3.

Furthermore, there are a plurality of the air outlets 204, and each of the air outlets 204 is connected to each of the guide grooves 208 and corresponds to each other. Specifically, the air outlets 204 and the guide grooves 208 in this embodiment are provided with four, respectively, the four air outlets 204 are grille openings, and the four air outlets 204 are distributed along the length direction of the heat dissipation bracket 201. The adjacent air outlets 204 are isolated from each other, and the four guide grooves 208 are arranged in layers along the up and down directions. The heat dissipation fin 202 in this embodiment includes two structural forms, the first one has four guide holes 209 as shown in FIG. 5, and the second one has two guide holes 209 as shown in FIG. 6. From top to bottom, the first guide hole 209 of the first heat dissipation fin 202 is used to communicate with the first guide groove 208 and the first air outlet 204 (the first one from left to right along the length direction of the heat dissipation bracket 201). The second guide hole 209 of the first heat dissipation fin 202 is communicated with the second guide groove 208 and the air outlet 204. The third guide hole 209 of the first heat dissipation fin 202 is communicated with the third guide groove 208, and the first guide hole 209 of the second heat dissipation fin 202 is communicated with the third guide groove 208 and the third air outlet 204 at the same time. The fourth guide hole 209 of the first heat dissipation fin 202 is communicated with the fourth guide groove 208 and the second guide hole 209 of the second heat dissipation fin 202 is communicate with the fourth guide groove 208 and the fourth air outlet 204 at the same time. The four air outlets 204 in this embodiment can discharge air at the same time, and the wind blown into the air inlet 203 by the fan 4 is divided into four parts. The first and second parts are used for the first heat dissipation fin 202 to dissipate heat, and the third and fourth parts are used for the second heat dissipation fin 202 to dissipate heat, so that each heat dissipation fin 202 dissipates heat evenly, improves the heat dissipation effect, and thus makes the cooling effect of various parts of the neck collar more uniform.

Furthermore, an installation compartment 103 is provided on the inner side of the neck collar bracket 1, the electric control component 7 is arranged in the installation compartment 103, and one end of the heat dissipation component 2 away from the air inlet 203 is connected to one side of the installation compartment 103. Specifically, the switch (not shown) of the electric control component 7 can be arranged outside the installation compartment 103, while the control circuit board (not shown) and the battery (not shown) of the electric control component 7 can be arranged in the installation compartment 103. One end of the two heat dissipation components 2 are respectively connected to the two sides of the installation compartment 103, so that the structure of the refrigerable hanging ice neck collar is more compact and stable.

The above description is only some embodiments of the present application, and does not limit the patent scope of the present application. All equivalent structural changes made by using the contents of the present application specification and drawings under the technical concept of the present application, or directly/indirectly applied in other related technical fields are included in the scope of the present application.

What is claimed is:

1. A refrigerable hanging ice neck collar, comprising:
an elastic neck collar bracket;
a heat dissipation component provided at the neck collar bracket and configured to form an internal air duct, wherein a side of the air duct is provided with a through hole, and the heat dissipation component is provided with an air inlet and an air outlet;
a refrigeration sheet provided at an external side of the heat dissipation component and configured to cover the through hole;
a fan provided at an end of the neck collar bracket and adjacent to the air inlet of the heat dissipation component, wherein an air outlet direction of the fan is oriented toward the air inlet;
an elastic non-metallic shell provided at an inner side of the neck collar bracket, wherein a portion of the non-metallic shell is connected to a side of the heat dissipation component, and the non-metallic shell is provided with a material filling part;
a cold storage material layer provided within the material filling part of the non-metallic shell, and configured to contact both the refrigeration sheet and an inner side of the non-metallic shell; and
an electric control component provided at the neck collar bracket and electrically connected to the refrigeration sheet and the fan,
wherein the heat dissipation component comprises a heat dissipation fin and a heat dissipation bracket;
the neck collar bracket is provided with a bayonet, and the heat dissipation bracket is provided at the inner side of the neck collar bracket;
the heat dissipation fin is provided within the bayonet and is configured to seal the bayonet, forming the air duct cooperatively with the neck collar bracket and the heat dissipation bracket; and
the heat dissipation fin is opposite to the through hole and the refrigeration sheet.

2. The refrigerable hanging ice neck collar according to claim 1, wherein:

the end of the neck collar bracket is provided with a protective shell for protecting the fan, and the protective shell is provided with an air intake side and an air exhaust side;

the air exhaust side of the protective shell is connected and communicated with one end of the heat dissipation component where the air inlet is provided; and the fan is provided within the protective shell, and the air outlet direction of the fan is toward the air exhaust side of the protective shell.

3. The refrigerable hanging ice neck collar according to claim 2, wherein the air intake side of the protective shell is provided with a steel mesh, and the fan is provided at a side of the steel mesh proximate to the air inlet.

4. The refrigerable hanging ice neck collar according to claim 3, wherein:

the refrigerable hanging ice neck collar comprises two fans, and the two fans are respectively provided at two ends of the neck collar bracket;

two heat dissipation components are provided at the neck collar bracket, and each of the two heat dissipation components is provided with a corresponding refrigeration sheet; and the air inlets of the two heat dissipation components respectively correspond to the two fans.

5. The refrigerable hanging ice neck collar according to claim 1, wherein a plurality of refrigeration sheets are evenly distributed on the heat dissipation component.

6. The refrigerable hanging ice neck collar according to claim 1, wherein a protrusion is provided at a side of the heat dissipation fin within the air duct, and the protrusion is configured to extend through the through hole and contact a side of the refrigeration sheet.

7. The refrigerable hanging ice neck collar according to claim 6, wherein along an air inlet direction of the air inlet, a plurality of guide grooves are provided at an inner side of the heat dissipation bracket, a plurality of guide holes are provided in the heat dissipation fin, and each guide hole is communicated with the corresponding guide groove.

8. The refrigerable hanging ice neck collar according to claim 7, wherein a plurality of air outlets are provided, and each of the air outlets is communicated with a corresponding airflow guide groove.

9. The refrigerable hanging ice neck collar according to claim 1, wherein an installation compartment is provided at an inner side of the neck collar bracket, the electric control component is provided within the installation compartment, and an end of the heat dissipation component away from the air inlet is connected to a side of the installation compartment.

\* \* \* \* \*